United States Patent
Krogh et al.

(10) Patent No.: US 11,549,948 B2
(45) Date of Patent: Jan. 10, 2023

(54) DETECTION METHOD AND MEANS THEREFOR

(71) Applicant: Mipsalus ApS, Hørsholm (DK)

(72) Inventors: Nicolas Otto Krogh, Virum (DK); Klaus Gregorius, Søborg (DK); Elena Fernandez Laborda, Frederiksberg (DK)

(73) Assignee: MIPSALUS APS, Hørsholm (DK)

( * ) Notice: Subject to any disclaimer, the term of this patent is extended or adjusted under 35 U.S.C. 154(b) by 203 days.

(21) Appl. No.: 16/084,460

(22) PCT Filed: Mar. 15, 2017

(86) PCT No.: PCT/EP2017/056059
§ 371 (c)(1),
(2) Date: Sep. 12, 2018

(87) PCT Pub. No.: WO2017/157980
PCT Pub. Date: Sep. 21, 2017

(65) Prior Publication Data
US 2020/0166516 A1    May 28, 2020

(30) Foreign Application Priority Data
Mar. 15, 2016 (EP) .................... 16160488

(51) Int. Cl.
*G01N 33/58* (2006.01)
*B01L 3/00* (2006.01)

(52) U.S. Cl.
CPC ............ *G01N 33/582* (2013.01); *B01L 3/508* (2013.01); *B01L 2300/0663* (2013.01); *B01L 2300/0861* (2013.01); *B01L 2300/0864* (2013.01); *B01L 2300/168* (2013.01); *G01N 2600/00* (2013.01)

(58) Field of Classification Search
CPC ..... B01L 2300/0663; B01L 2300/0861; B01L 2300/0864; B01L 2300/168; B01L 3/508; G01N 2600/00; G01N 33/53; G01N 33/542; G01N 33/582
See application file for complete search history.

(56) References Cited

U.S. PATENT DOCUMENTS

| | | | |
|---|---|---|---|
| 2009/0110601 A1 | 4/2009 | Levi et al. | |
| 2010/0312483 A1* | 12/2010 | Peyser ................... | G01N 33/66 702/19 |
| 2012/0171154 A1* | 7/2012 | Krogh ................... | B01J 20/268 424/78.17 |

FOREIGN PATENT DOCUMENTS

| WO | WO 1993/001498 | 1/1993 |
|---|---|---|
| WO | WO 2005/068980 | 7/2005 |
| WO | WO 2005/075995 | 8/2005 |
| WO | WO 2007/095949 | 8/2007 |
| WO | WO 2009/083975 | 7/2009 |
| WO | WO 2010/141888 | 12/2010 |
| WO | WO 2011/033021 | 3/2011 |
| WO | WO 2013/127433 | 9/2013 |
| WO | WO 2014/181662 | 11/2014 |

OTHER PUBLICATIONS

Reply to International Search Opinion for PCT/EP2017/056059 dated Mar. 12, 2018.*
Descalzo et al., "Luminescent Core-Shell Imprinted Nanoparticles Engineered for Targeted Förster Resonance Energy Transfer-Based Sensing,"Anal. Chem., 2013, vol. 85, No. 11, pp. 5316-5320.*
My PKU Binder, National PKU Alliance (USA), Chapter 3: Monitoring Blood Phenylalanine levels, 2011, pp. 26-30.*
Varghese et al., "FRET for lab-on-a-chip devices—current trends and future prospects," Lab Chip, 2010, vol. 10, pp. 1355-1364.*
Urraca et al., "Molecularly Imprinted Polymers as Antibody Mimics in Automated On-Line Fluorescent Competitive Assays," Anal. Chem., 2007, vol. 79, No. 13, pp. 4915-4923.*
Chen et al., "Molecularly Imprinted Polymer as an Antibody Substitution in Pseudo-immunoassays for Chemical Contaminants in Food and Environmental Samples," J. Agric. Food Chem., 2018, vol. 66, No. 11, pp. 2561-2571.*
Vlatakis et al., "Drug assay using antibody mimics made by molecular imprinting," Nature, 1993, vol. 361, pp. 645-647.*
Hunt et al., "A fluorescence polarisation molecular imprint sorbent assay for 2,4-D: a non-separation pseudo-immunoassay," Chem. Commun., 2006, pp. 1754-1756.*
Ye et al., "Polymers Recognizing Biomolecules Based on a Combination of Molecular Imprinting and Proximity Scintillation: A New Sensor Concept," J. Am. Chem. Soc., 2001, vol. 123, No. 12, pp. 2901-2902.*
Bedwell, T.S., Whitcombe, M.J. "Analytical applications of MIPs in diagnostic assays: future perspectives," Anal. Bioanal. Chem., 2016, vol. 408, pp. 1735-1751; Published online: Nov. 21, 2015.*
Alexander, C. et al., "Molecular imprinting science and technology: a survey of the literature for the years up to and including 2003", Journal of Molecular Recognition, 19, (2006), pp. 106-180.
International Search Report and Written Opinion for International Application No. PCT/EP2017/056059 dated Jun. 19, 2017.
International Preliminary Report on Patentability Chapter II for International Application No. PCT/EP2017/056059 dated Aug. 2, 2018.
European Communication Pursuant to Article 94(3) EPC for European Application No. 17710737.2 dated Feb. 15, 2022.
Vasapollo et al., "Molecularly Imprinted Polymers: Present and Future Prospective," Int. J. Mol. Sci., 12:5908-5945 (2011).

* cited by examiner

*Primary Examiner* — Galina M. Yakovleva
(74) *Attorney, Agent, or Firm* — Alston & Bird LLP

(57) ABSTRACT

Disclosed is a FRET based assay and related products. The assay employs molecular imprinted polymers having a very high affinity for their target.

17 Claims, 3 Drawing Sheets

DETECTION METHOD AND MEANS THEREFOR

CROSS-REFERENCE TO RELATED APPLICATION(S)

This application is a U.S. National Stage entry of International Application No. PCT/EP2017/056059 filed Mar. 15, 2017, which claims the benefit of European Patent Application No. 16160488.9, filed Mar. 15, 2016, each of which is herein incorporated by reference in its entirety for all purposes.

FIELD OF THE INVENTION

The present invention relates to the field for diagnostics and probing. In particular the present invention relates to the field of sensitive determination of analytes in samples.

BACKGROUND OF THE INVENTION

Molecular Imprinted Polymers, MIPs, are products that have been developed to produce synthetic receptor entities that bind an epitope similar to the way an antibody binds an antigen (Alexander et al. 2006). Such MIPs have typically been employed in chromatographic methods, but they have also been suggested as pharmaceutical products due to their functional equivalency with antibodies.

OBJECT OF THE INVENTION

It is an object of embodiments of the invention to provide a method for simplified detection of the presence and/or quantity and/or concentration of analytes, in aqueous solutions generally and in body fluids particularly.

LEGENDS TO THE FIGURE

Figure 1:
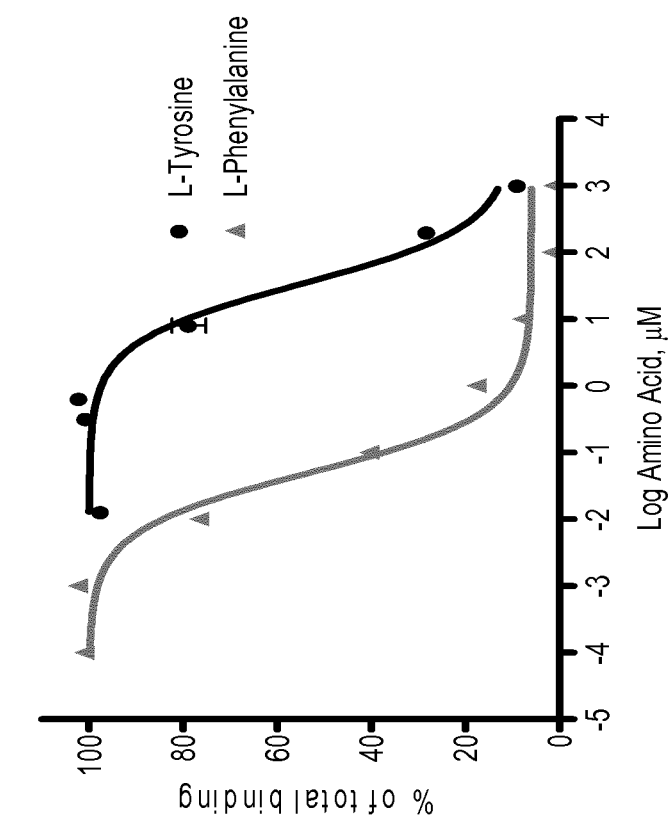
Figure 1:
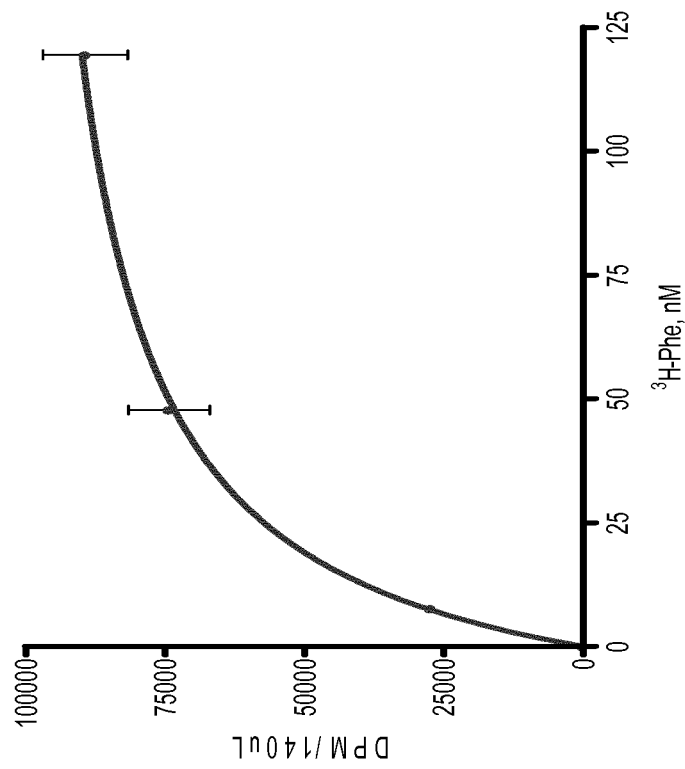

FIG. 1: Graphs showing binding characteristics of Phe-binding MIPs using $^3$H-labelled L-phenylalanine ($^3$H-Phe).

Figure 2:
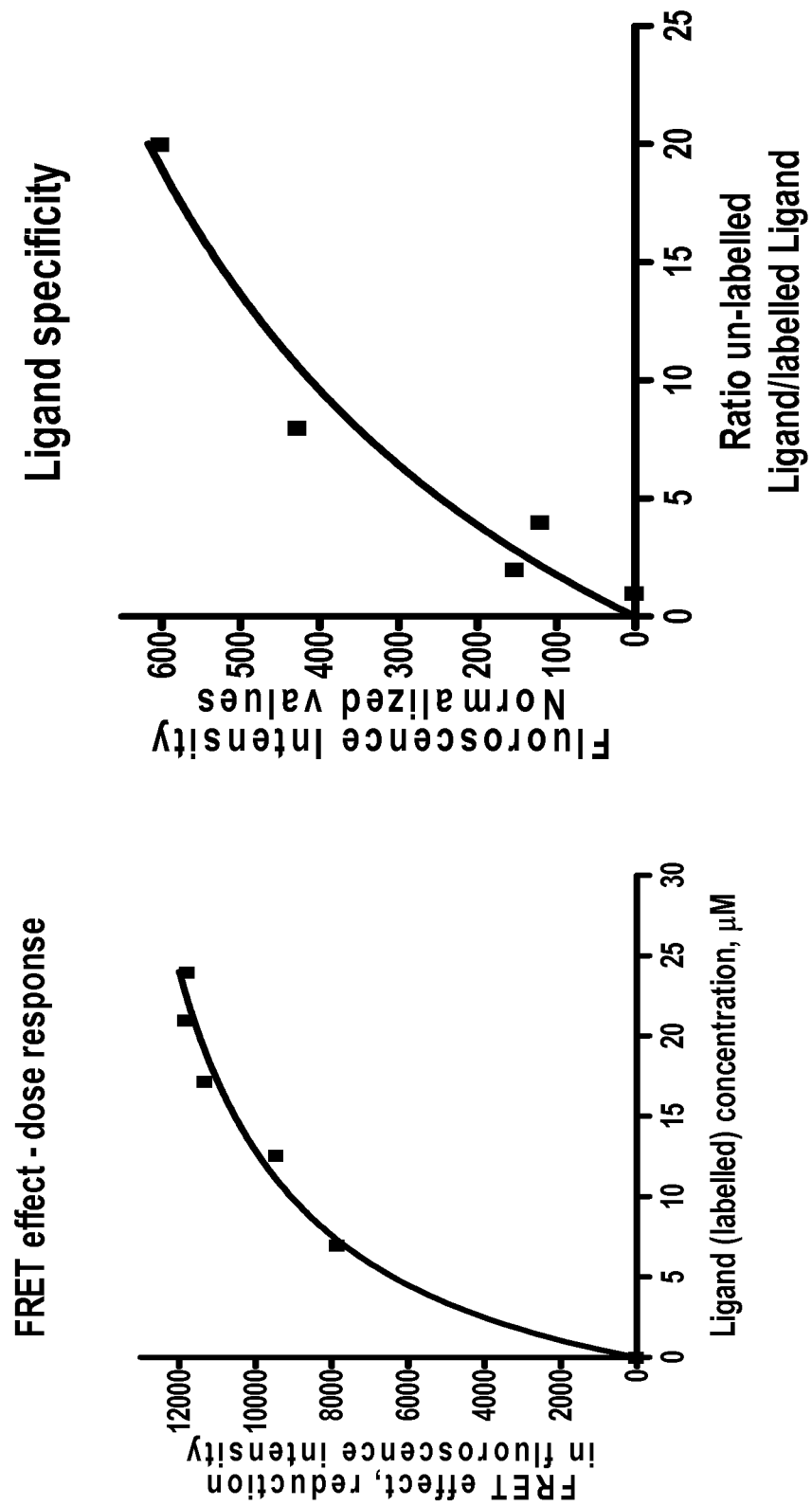

FIG. 2: Graphs showing the fluorescence intensity of Phe binding MIPs labelled with fluorescein incubated with a ligand made of dextran conjugated with Phe and the dye QSY7 in different concentrations.

Figure 3:
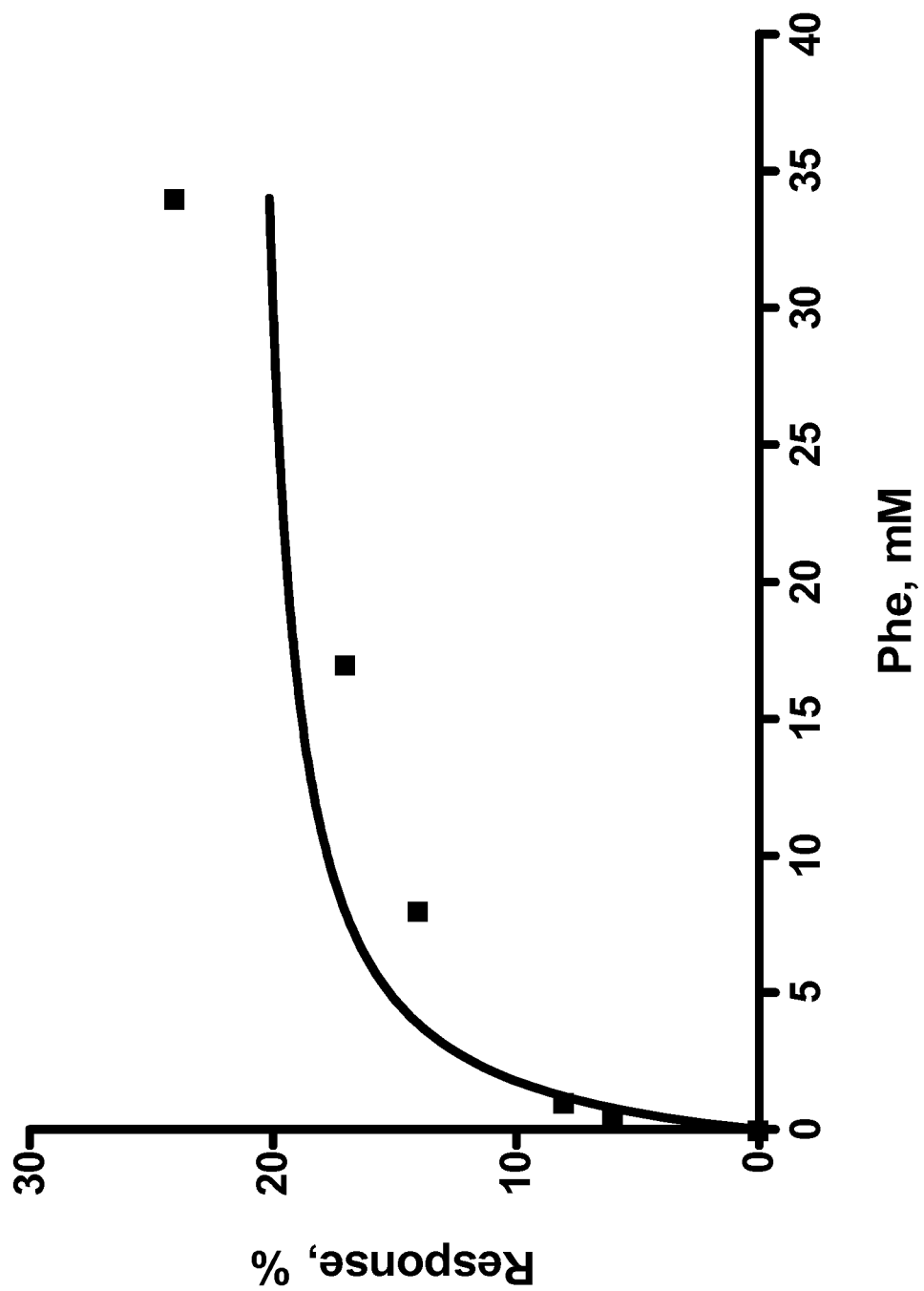

FIG. 3: Graph showing results of titration of L-Phe to a fixed volume of buffer containing fixed concentrations of Phe-binding MIPs conjugated with a fluorophore and a macromolecular ligand conjugated with L-Phe as well as a dye.

DESCRIPTION OF THE INVENTION

The present assignee has previously developed technology that has refined the general MIP preparation technology by considerably improving the binding properties of MIP compositions (WO 2007/095949, WO 2011/033021, and WO 2013/127433). By employing these technologies, the assignee has developed MIPs that bind L-phenylalanine ("L-Phe" or "Phe") with very high affinity and very high specificity by selecting the best binding MIPs particles (see FIG. 1). The plot in FIG. 1 shows that the Phe-binding MIPs binds Phe with a $K_d$ of approximately 21 nM and that the $EC_{50}$ value for Phe is more than 500 times lower than $EC_{50}$ for L-Tyrosine, meaning that interference from e.g. tyrosine is very limited.

In the present context, "molecular imprinted polymers" ("MIPs") are products of polymerized, cross-linked polymers that include voids to which a target molecule will bind. Typically, MIPs are obtained by a process where a template agent (typically, but not necessarily identical to the target) is present together with monomers and cross-linking agents during the polymerization process. After this, template is extracted and the polymerized material is micronized so as to expose the target-binding voids.

It has been found by the present inventors that due to the very high affinity and very high specificity of the detecting entity (the MIPs) produced according to the principles provided in WO 2007/095949, WO 2011/033021, and WO 2013/127433, whole blood analysis without any other pre-processing means than simple dilution has become possible. Further, the principles demonstrated in the context of determination of Phe concentration in blood are generally applicable to other analytes of interest from various sources and materials.

The Phe binding MIPs, which are used as exemplary in the present application, can be used to produce a sensor for detecting Phe in whole blood from patients suffering from hyperphenylalaninemia (HPA). The sensor product can be operated by the patient, a so-called home sensor.

The detection system can for instance be based on Fluorescence Resonance Energy Transfer, FRET, (also known as Förster Resonance Energy Transfer).

A FRET system of the present invention requires that a receptor (the MIPs) and a ligand are each supplied with a chromophore, which in turn are in the form of a donor and an acceptor or vice versa. The donor and acceptor should have appropriate spectral properties to act as a so-called FRET pair (Lakowicz, J. R.). The ligand will typically—but not necessarily—be constituted by a larger carrier molecule, e.g. dextran, which is conjugated with one or more epitope molecules (in the exemplified case phenylalanine) as well as a chromophore (typically a fluorophore or a dye). When the MIPs and ligand interact, the distance between the donor and the acceptor coupled to the MIPs and ligand, respectively, will on average be shorter than if they do not interact. This shorter distance will lead to a reduction of the fluorescence intensity from the donor (and a shorter lifetime of the electrons in the exited state in the donor) due to transfer of energy from the exited electrons in the fluorophore molecule to the dye molecule—the so-called FRET effect.

If free molecules capable of binding the MIPs are added to such a system they will be able to compete with the ligand for binding to the MIPs. Consequently, increasing concentrations of free epitope will accordingly reduce the MIPs-ligand interaction and reduce the FRET effect and hence result in increased fluorescence intensity from the donor. This increase in fluorescence can in turn be correlated to the concentration of free epitope.

Coupling of the fluorophore or dye to the MIPs or ligand can be achieved by conventional coupling chemistry. In the example presented in FIG. 2, the fluorophore is fluorescein, which was coupled to the Phe-binding MIPs by initially supplying the MIPs with primary amino groups by activating the carboxylic groups in the MIPs with N-(3-Dimethylaminopropyl)-N'-ethylcarbodiimide (EDC) and N-Hydroxysuccinimide (NHS) followed by addition of an excess of 1,5-diaminopentane (cadaverine; un-coupled cadaverine was subsequently removed by dialysis), and subsequently using the (now present) primary amino groups on the MIPs for coupling of the donor fluorophore. The polymer of which the MIPs in this case was constituted was in the form of cross-linked methacrylic acid (MAA) polymer that provided the carboxylic groups that were derivatized.

Another way to incorporate a chromophore in the MIPs would be to add the chromophore as a polymerizable monomer to the pre-polymerization solution when preparing the MIPs. An example of such a polymerizable chromophore is Fluorescein o-acrylate (Cas #193419-86-2) which is supplied with an allyl group, and therefore will co-polymerize with the other monomers.

The ligand in the examples was prepared by activating dextran with Divinyl Sulfone (DVS, Lihma et al. 1993)) and subsequent addition of Phe and $NH_3$. The dextran molecules then contains both Phe, coupled via the α-amine, and primary amino groups from $NH_3$ reacting with the sulfone. Subsequently, dye or fluorophore can be coupled via these amino groups in a manner corresponding to the above described coupling to the amino groups in the MIPs.

As will appear from the present disclosure, it is preferred that also the ligand is in the form of a very stable material because this facilitates those embodiments, where a sensor device of the present invention is can be used for multiple determination without the need for exchange of the ligand.

As a consequence of the results obtained the present inventors have realised that the method described for the Phe assay is equally applicable to other analytic methods where other analytes are to be determined. This generic version of the presently presented method is presented in the claims and discussed below.

DETAILED EMBODIMENTS

One embodiment of the invention relates to a method for qualitative or quantitative determination of the presence of an analyte in a sample, comprising
1) adding the sample to a composition comprising a) molecular imprinted polymers (MIPs) that bind the analyte and b) a ligand, which competes with said analyte for binding to said MIPs,
2) measuring reduction in binding of the ligand to the MIPs upon addition of the sample, and
3) determining qualitatively or quantitatively the presence of the analyte in the sample by correlation with the reduction measured in step 2.

Typically, the MIPs comprise a first chromophore (typically a fluorophore), which may either be included in the MIPs during preparation of the polymer (cf. above), or instead be coupled to the polymer via suitable reactive groups, such as the carboxylic groups of methacrylic acid. Also the ligand is typically labelled, conveniently by letting the label be a second chromophore, such as a fluorophore or a dye that constitutes a Fluorescense Resonance Energy Transfer (FRET) pair with the first chromophore of the MIP. However, the ligand could also comprise the first chromophore and the MIPs the second chromophore. In case the second chromophore is a fluorescent dye, the energy transferred from the donor (first chromophore) to the acceptor (second chromophore) could be measured as a change in fluorescence intensity from the second chromophore.

So in important embodiments of the method the MIPs comprise the first chromophore defined above and the ligand comprises the second chromophore defined above so that one of the first and second chromophores acts as a donor and the other chromophore acts as an acceptor in a FRET system. This in turn allows the qualitative or quantitative detection of the analyte by correlating with the change in intensity of radiation emitted from the donor chromophore—or in the event the acceptor chromophore is itself a fluorophore, then correlating with the change in intensity of radiation emitted from the acceptor chromophore. Alternatively, the transferred energy between the chromophores comprising the FRET pair could be detected as change in fluorescence life time of the first fluorophore (see Lakowich (1999), Principles of Fluorescence Spectroscopy, second edition, Kluwer Academic/Plenum Publishers).

Useful "FRET pairs" are according to the invention any of the following non-limiting examples:

| Donor | Acceptor(s) |
|---|---|
| Fluorescein | QSY® 7 or QSY® 9 |
| Alexa Fluor® 594 | HMCV dyes described in WO 05/059037 |
| | Malachite green |
| | QSY® 21 |
| Alexa Fluor® 350 | Dabcyl |
| Alexa Fluor® 405 | QSY® 35 |

QSY® 7 (carboxylic acid, succinimidyl ester):

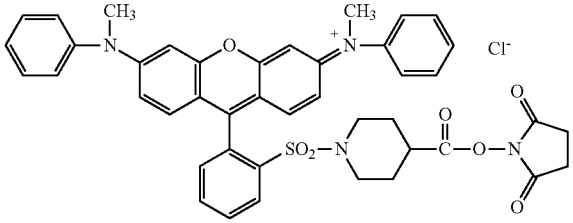

QSY® 7 (C5-maleimide)

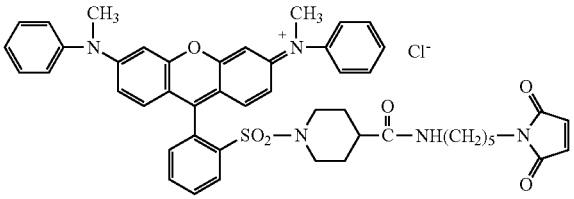

QSY® 9 (carboxylic acid, succinimidyl ester):

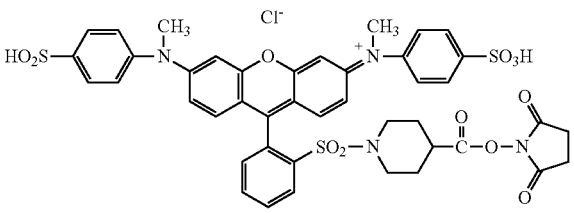

QSY 9® (C5-maleimide):

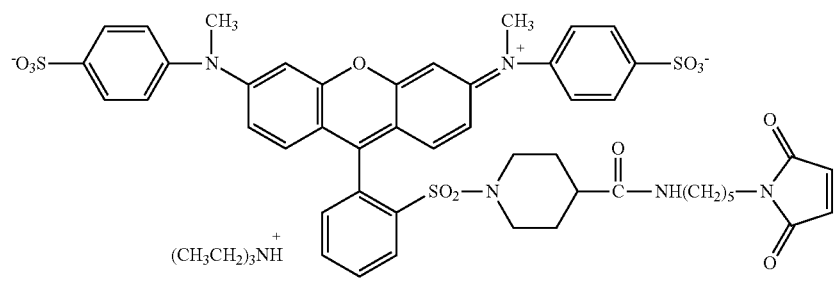

QSY® 21 (carboxylic acid, succinimidyl ester):

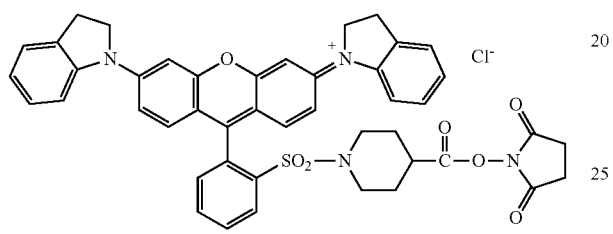

QSY® 35:

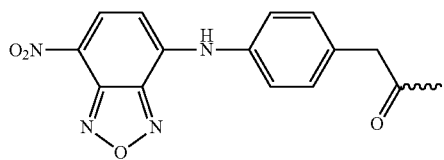

Alexa Fluor® 594 (succinimidyl ester):

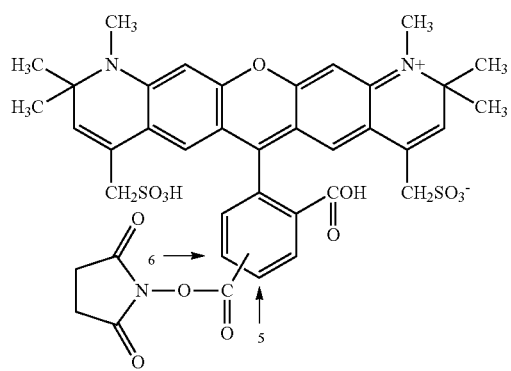

Alexa Fluor® 350 (succinimidyl ester):

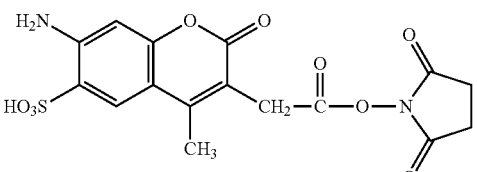

Alexa Fluor® 405 (succinimidyl ester):

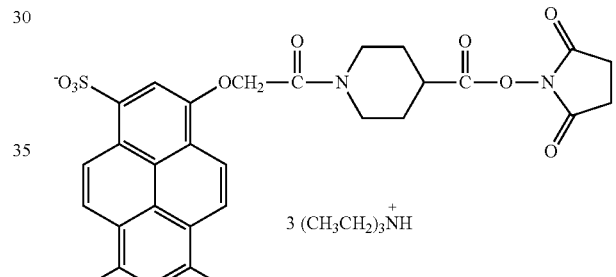

Dabcyl:

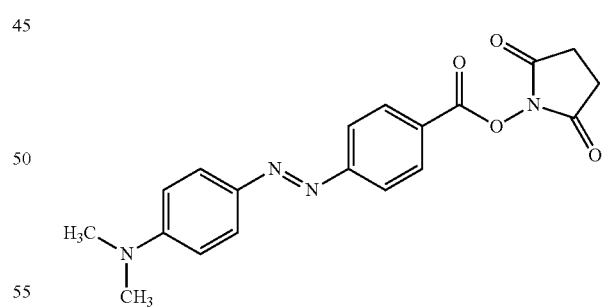

Instead of Phe, as mentioned above, other analytes could be any molecule existing in the body fluids. Since MIPs can be prepared with virtually any template molecule and since the present inventors have prepared MIPs of hitherto unseen affinity for their target molecules, the exact choice of analyte is inessential.

Non-limiting examples of analytes are selected from the group consisting of an amino acid, glucose, lactic acid, creatinine, creatine, creatine phosphate, a drug substance, a body fluid substance, and an environmentally relevant substance from water or industrial production fluids. An amino acid analyte is typically selected from the L-amino acids alanine, cysteine, aspartic acid, glutamic acid, phenylalanine, glycine, histidine, isoleucine, lysine, leucine methionine, asparagine, proline, glutamine, arginine, serine, threonine, valine, tryptophan, and tyrosine. Phenylalanine and tyrosine are due to their clinical relevance particularly preferred.

In general, an analyte of interest can be any substance that can effectively function as template in preparation of MIP particles. In some cases even a derivative of the analyte can work as template in the preparation of MIPs. This opens the possibility of determining the presence or concentration of analytes by use of the presently disclosed technology in a wide range of environments and settings. This is all the more relevant, since an attractive feature of the invention is the inherent stability of MIPs, which allows for the repeated use of the labelled MIPs if they are used in a system that allows for repeated washing off of bound analyte. Practice of the invention will under such circumstances merely require that the MIPs are contacted with fresh ligand as well as the sample that potentially contains the analyte, subsequent determination of the presence/concentration/amount of the analyte as disclosed herein, and washing/cleansing of the MIPs whereby bound analyte and ligand is removed. After this process, the MIPs can once again be subjected to ligand and sample for testing. In such a setting, the MIPs can be situated in a separate compartment in the test environment, meaning that it is only necessary to supply ligand and sample into the separate compartment each time a measurement has to be made. This obviates the need for taking out samples and also for repeated exchange of specific detection means for the analytes as would be the case if the analyte were to be determined using an immune assay.

Non-limiting examples of analytes and sample environments are:

1) Analytes that constitute metabolites and/or expression products from industrial fermentation processes can be determined according to the present invention, thereby allowing effective control of the fermentation process based on measured concentration/amount of the analyte(s). Such analytes can be metabolic by-products that interfere with the efficacy of fermentation, or they can be intended products of the fermentation. Thereby, nutrients, pH, temperature, salinity and other physicochemical conditions in a fermentation can be adjusted. Analytes of interest in such a setting are, depending on the fermentation setting, carbon sources (sucrose, lactose, fructose, glucose, raffinose, maltose, maltodextrins), nitrogeneous compounds (urea, uric acid, amino acids, amino nitrogen compounds, peptides, nitrates, nitrites), vitamins, pigments, biotin, lactic acid, pyrodexine, citric acid, pyrazines etc.

2) Analytes that constitute undesired pollutants in environmental or drinking water, such as toxic organometallic compounds (such as methylmercury, stannanes etc); bacterial toxins; pesticides; disinfection byproducts such as bromate, chlorite, haloacetic acids, and trihalomethanes; disinfectants (chloramines, chlorine, and chlorine dioxide); inorganic chemicals (e.g. antimony, arsenic, barium, beryllium, cadmium, chromium, copper, cyanide, fluoride, lead, nitrite, selenium, thallium); organic chemicals (such as acrylamide, alachlor, atrazine, benzene, Benzo(a)pyrene (PAHs), Carbofuran, Carbon tetrachloride, Chlordane, Chlorobenzene, 2,4-D, Dalapon, 1,2-Dibromo-3-chloropropane (DBCP), o-Dichlorobenzene, p-Dichlorobenzene, 1,2-Dichloroethane, 1,1-Dichloroethylene, cis-1,2-Dichloroethylene, trans-1,2-Dichloroethylene, Dichloromethane, 1,2-Dichloropropane, Di(2-ethylhexyl) adipate, Di(2-ethylhexyl) phthalate, Dinoseb, Dioxin (2,3,7,8-TCDD), Diquat, Endothall, Endrin, Epichlorohydrin, Ethylbenzene, Ethylene dibromide, Glyphosate, Heptachlor, Heptachlor epoxide, Hexachlorobenzene, Hexachlorocyclopentadiene, Lindane, Methoxychlor, Oxamyl (Vydate), Polychlorinated biphenyls (PCBs), Pentachlorophenol, Picloram, Simazine, Styrene, Tetrachloroethylene, Toluene, Toxaphene, 2,4,5-TP (Silvex), 1,2,4-Trichlorobenzene, 1,1,1-Trichloroethane, 1,1,2-Trichloroethane, Trichloroethylene, Vinyl chloride, and Xylenes).

3) Analytes present in industrial waste water—any of the above-mentioned pollutants are relevant in this connection.

4) Analytes present in hospital waste water—in particular various drugs such as antibiotics and cytostatic agents.

5) Analytes present in blood and other body fluids (such as amniotic fluid, aqueous humour, vitreous humour, bile, blood serum or other blood components, breast milk, cerebrospinal fluid, cerumen, chyle, chyme, endolymph, perilymph, exudates, diarrheal feces, female ejaculate, gastric acid, gastric juice, lymph, mucus, pericardial fluid, peritoneal fluid, pleural fluid, pus, rheum, saliva, sebum, serous fluid, semen, smegma, sputum, synovial fluid, sweat, tears, urine, vaginal secretion, and vomit). In such a setting, a device comprising MIPs useful in the invention could be permanently implanted to allow repeated or continuous measurements; this is in addition to more traditional blood sample sampling and subsequent analysis according to the present invention. Analytes in this context could be any one of creatinine, blood urea nitrogen, bilirubin, aspartate transaminase (ast), alanine transaminase (alt), gamma-glutamyl transpeptidase (ggt), alkaline phosphatase (alp), h-FABP, troponin, myoglobin, CK-MB, B-type natriuretic peptide (BNP), transferrin, TIBC, vitamin B12, vitamin D, folic acid, glucose, C-reactive protein, Glycated hemoglobin (HbA1c), urea, uric acid, adrenocorticotropic hormone (ACTH), toxins, and neuron-specific enolase. A device of this type could e.g. include a detection means described below, in particular a detection means where both MIPs and ligand are confined whereas the analyte can either 1) be added, determined, liberated and removed or 2) continuously monitored because the ligand freely can enter and leave the detection means.

A drug analyte subjected to the present invention can be selected from warfarin, dopamine, paracetamol, digitoxin, morphine, heroin, cocaine, tetrahydrocannabinol (THC), amphetamine, and metamphetamine, but any substance, be it a pharmaceutical, a drug or a toxic substance can in practice be determined by means of the present invention.

Determination in step 3 is often performed by measuring light emitted, in particular light emitted from the donor discussed above; in such embodiments measurement is conveniently performed with a spectrophotometer, such as a fluorometer.

It will be understood that the preferred embodiments all utilise those MIPs where all or essentially all MIPs in the composition exhibit specific binding of the analyte.

As mentioned above, the ligand may be in the form of a larger molecule, but alternatively it is a soluble substance quasi-identical to the analyte. So the ligand can for instance be selected from a molecule identical to the analyte or a fragment thereof or a mimic thereof, directly coupled to a label, a molecule identical to the analyte of a fragment thereof or a mimic thereof, coupled to a larger carrier molecule to which is also coupled a label, and a molecule identical to the analyte or a fragment thereof or a mimic thereof, coupled to both a larger carrier molecule and to a label, wherein the label is as described herein. The larger carrier molecule is typically a polysaccharide such as dextran. In embodiments of importance, the carrier is constituted by a material that exhibits a stability comparable to that of the MIPs—e.g. by having a carrier prepared from the same materials as the MIPs, but leaving out template conforming voids. In this case, the carrier is conveniently micronized to sizes in the low μm or the nm size range.

The MIPs have a stability that allow that they are used multiple times for determination of the analyte when practising the method of the invention. Hence, this entails that a determination of an analyte is followed by a step of liberation of ligand and analyte from the MIPs so as to enable repeated use. In certain of these embodiments the ligand is only liberated but not removed from the reaction compartment comprising the MIPs. In yet further embodiments, the analyte can move freely to and from contact with the compartment comprising MIPs and ligand, whereas the latter two remain confined to the compartment; this requires use e.g. filters or the like that allow passage of the analyte but retain MIPs and ligand. Also, either the ligand or the MIPs may be coupled to a solid stationary phase.

So the method of the invention may be carried out multiple times using the same MIPs, i.e. the invention includes embodiments wherein the MIPs are used multiple times for determination of the same type of analyte. Typically each step of analysis (determination of analyte) is followed by a step of liberation of ligand and analyte from the MIPs so as to enable repeated use. However, the invention also enables continuous determination where analyte is continuously or intermittently brought in contact with the MIP/ligand system. When such a system is designed to retain the MIPs and the analyte in a confined space while allowing analyte to freely accessing and leaving the space, dynamic determination of analyte can be achieved. This is particularly of interest in permanently positioned or implanted devices used for monitoring analyte.

Thus, an embodiment of the present invention includes that the MIPs are present in a compartment that comprises an inlet for sample and optionally an inlet for ligand, means for liberating ligand and sample from the MIPs, and at least one outlet for liberated sample and optionally for liberated ligand; the latter depends on whether the method of the invention "recycles" both the ligand and the MIPs or only the MIPs. In case the inlet and outlet only allows passage of the analyte, the MIPs and the ligand are said to be in a confined space.

This means that an embodiment utilises MIPs with a chromophore attached/incorporated, and the ligand with a chromophore attached/incorporated, together in a container with a liquid, e.g. a test sample, where the MIPs and ligand can interact, and where the MIPs and the ligand have a molecular size, shape, charge or other physical feature that makes it possible to retain both the MIPs and the ligand in the container when the liquid is replaced, by e.g. washing the compartment/container or to replace the sample for a new test. Means of such detention could e.g. be a filter, semipermeable membrane or ionic exchange matrix.

Another embodiment involves the use of a container were the ligand, including the attached chromophore, is immobilized on the walls or a structure inside the container and the MIPs are in suspension, so that a relatively simple filter could be used to retain the MIPs while washing the container or replacing the sample. Also this embodiment could be reversed by having the MIPs linked to the walls or internal structure in the container and having the ligand in suspension or in solution.

In the practice of some embodiments of the invention, a practitioner or a patient may draw a small blood sample and introduce this into a sensor means of the present invention (see below) to allow reaction between MIPs, analyte and ligand until equilibrium is reached (typically within a few seconds or a few minutes). After this, the sensor means is positioned in a reader unit (typically a fluorometer), which applies electromagnetic radiation (typically light) of the excitation wavelength of the donor chromophore. The readout is—when the acceptor is a dye that does not fluoresce— the intensity of light of the fluorescent light from the donor—if the intensity is low, no or little competition between the analyte and the ligand has been observed, meaning that the concentration of analyte is low. In contrast, a high intensity signifies the presence of a higher concentration of analyte. In embodiments where the acceptor is itself a fluorophore, the increase in donor fluorescence is accompanied by a decrease in acceptor fluorescence. This means that it alternatively or as an add-on is possible to determine the change in the acceptor fluorescence, where a decrease signifies binding between analyte and MIPs.

In some embodiments it may be convenient to mix the ligand and the analyte prior to subsequent admixture with MIPs. Also in some embodiments, the mixture of MIPs and analyte is made prior to mixture with the ligand. These embodiments may be relevant in those cases where the binding between ligand and MIPs is so strong that the time needed to reach true equilibrium is limiting. This problem can be over come by contacting the unbound MIPs with a mixture of ligand and analyte, or in rarer cases by contacting MIPs bound to analyte with the ligand. In those cases, one possibility is to admix the ingredient in two separate devices, but a more convenient way is to let the sensor means comprise at least two compartments, where one can receive the sample and allow pre-mixing and where the second can contain the remaining ingredients. By including a barrier, which can be destroyed or rendered permeable, between the two compartments the final mixing can be attained.

Sensor Means/Device of the Invention

Another embodiment of the present invention relates to a sensor means (or sensor device) comprising a container, having a cavity including MIPs that are capable of binding an analyte, where said MIPs are labelled with a first chromophore, and a ligand that is capable of competing with the analyte for binding to the MIPs, where the ligand is labelled with a second chromophore, and optionally a solvent, wherein the first and second chromophores constitute the donor and acceptor in a FRET pair, and wherein the container is permeable for radiation (e.g. light) emitted by the donor or wherein the container comprises a photosensor capable of detecting radiation emitted by the donor and comprises means for transmitting a signal from said photosensor to a processing means.

As indicated the container need not be light permeable— instead a photosensor may be present inside the container/ cavity (which functions as a reaction chamber where analyte can bind MIPs) so as to allow detection of radiation emitted by the donor. This embodiment thus requires that the sensor means comprises means for transmission of a signal from the photosensor to a means that can process the signal, after which it can be converted into a readable output for an end user. This embodiment is in particular useful when the sensor means is installed or implanted for a prolonged period of time so as to allow repeated determinations of analyte—in some environments, a radiation permeable material may loose transparency, whereas a radiation sensor can be cleaned as part of the process of preparation for a new determination.

The solvent is optional: both the MIPs and the ligand may be in dry form (such as freeze dried), and rendered soluble/suspended by the addition of a liquid sample such as blood. However, if the solvent is present, it typically comprises at least one haemolytic agent (when the sample to be tested is blood or a blood component) and/or buffer and/or salts. These ingredients may also be present in dry form if no solvent is present.

As mentioned above, the simplest version of the present embodiment of the invention is a sensor means as described above, wherein the container contains the MIPs and the ligand and the optional solvent and other agents in the same compartment of the cavity. But if there is a need to ensure premixing of some reactants, the container may contain the MIPs and the ligand in two separate compartments of the cavity, wherein the compartments are separated by a separation element (a barrier) that can be removed or rendered permeable to allow admixture of the contents of the two separate compartments. Typically, such a barrier can be a breakable wall, but it could also be a soluble wall that is dissolved by the addition of the sample.

To allow easy entry of the sample into the sensor means, it will typically comprise an entry port or inlet (e.g. an injection membrane known per se) that allows introduction of a sample comprising an analyte into the compartment that comprises the ligand and/or into the compartment that comprises the MIPs and/or into the compartment that comprises both ligand and MIPs.

A light permeable container is typically made from—or has a window made from—a material selected from glass, quartz, and plastic that is permeable for radiation emitted by the donor.

The sensor means according to the present invention can utilise any of the MIPs described in detaile herein together with any of the ligands disclosed herein, meaning that all disclosures made herein in relation to the method of the invention applies mutatis mutandis to the detection means of the invention.

For instance, the sensor means of the invention can comprise a compartment that comprises an inlet for sample and optionally an inlet for ligand, means for liberating ligand and sample from the MIPs, and at least one outlet for liberated sample and optionally for liberated ligand. In certain embodiments, ligand and MIPs are confined to said compartment.

Kit of the Invention

Finally, the invention also relates to a kit comprising a sensor means as disclosed herein, at least one hypodermic needle, at least one means for temporarily holding a defined volume of a body fluid, and optionally a reader unit. The means for temporarily holding the defined volume of a body fluid is typically a capillary tube but may also be a simple syringe, and the reader unit is typically a spectrophotometer such as a fluorometer.

General Considerations Concerning the Invention

In all embodiments of the invention, it is preferred that the MIPs in the composition used all are ones the specifically bind the analyte. This means the MIP composition is substantially free from MIPs that are not capable of specific binding to the analyte; such MIPs can e.g. be prepared/obtained according to the methods disclosed in any one of WO 2007/095949, WO 2011/033021, and WO 2013/127433.

EXEMPLIFICATION

FIG. 1: Binding characteristics of Phe-binding MIPs using $^3$H-labelled L-phenylalanine (3H-Phe).

$^3$H-Phe was mixed with MIPs suspended in phosphate buffered saline (PBS), pH 8.0, and after incubation filtrated in a centrifuge filter device with a molecular cut off on 30 kDal allowing $^3$H-Phe not bound by MIPs to pass. The filtrate was mixed with scintillation fluid, counted on a scintillation counter. The counted value was subtracted from counted value of the total amount of $^3$H-Phe to calculate the amount of $^3$H-Phe bound by the MIPs. By plotting varying concentration of $^3$H-Phe and plotting the $^3$H-Phe concentration against the binding, the affinity could be calculated. In this example the $K_d$ was 21 nM (see the left graph). The graph to the right shows the results of a competitive binding experiments where varying amounts of L-Phe or L-tyrosine (L-Tyr), respectively, were added at a fixed concentration of MIPs and $^3$H-Phe and after incubation, filtrated and counted, to calculate the inhibitory effect of L-Phe and L-Tyr, respectively. $EC_{50}$ values were determined to be 50 nM for L-Phe and 34,000 nM for L-Tyr.

FIG. 2: The fluorescence intensity of Phe binding MIPs labelled with fluorescein incubated with a ligand made of dextran conjugated with Phe and the dye QSY7 in different concentrations. The graph to the left shows the reduction in fluorescence intensity (numerical values) as a function of increasing concentration of ligand indicating that the ligand and MIPs interact. The graph to the right shows that the MIPs-ligand interaction is specific to the ligand, since increasing ratio of ligand without dye (QSY7) results in increased fluorescent intensity.

FIG. 3: Titration of L-Phe to a fixed volume of buffer containing fixed concentrations of Phe-binding MIPs conjugated with a fluorophore and a macromolecular ligand having L-Phe as well as a dye conjugated.

The mixture was read in a fluorometer. Increasing concentration of L-Phe (x-axis) leads to increasing displacement of the ligand resulting in increasing fluorescence intensity (y-axis). The response on the y-axis refers to increase in intensity from the lowest intensity, i.e. with no L-Phe.

LIST OF REFERENCES

Alexander et al (2006) J Mol Recogn 19; 106-180
Lakowicz, J. R., Principles of Fluorescence Spectroscopy, Sec Ed. (1999), Kluwer Academic/Plenum Publishers
Lihma et al (1993) WO1993001498 A1

The invention claimed is:

1. A method for qualitative or quantitative determination of the presence of an analyte in a sample, comprising
   1) adding the sample to a composition comprising a) molecular imprinted polymers (MIPs) in suspension that bind the analyte and b) a ligand, which competes with said analyte for binding to said MIPs,
   2) measuring reduction in binding of the ligand to the MIPs upon addition of the sample, and
   3) determining qualitatively or quantitatively the presence of the analyte in the sample by correlation with the reduction measured in step 2), wherein the analyte is L-phenylalanine, and wherein the $EC_{50}$ value for L-phenylalanine is more than 500 times lower than the $EC_{50}$ for L-tyrosine.

2. The method according to claim 1, wherein the MIPs comprise a first chromophore.

3. The method according to claim 2, wherein the first chromophore is a fluorophore.

4. The method according to claim 1, wherein the ligand comprises a label.

5. The method according to claim 4, wherein the MIPs comprise a first chromophore, and the label is a second chromophore that constitutes a Fluorescence Resonance Energy Transfer (FRET) pair with the first chromophore.

6. The method according to claim 5, wherein the ligand comprises the second chromophore so that one of the first and second chromophores acts as a donor and the other chromophore acts as an acceptor.

7. The method according to claim 6, wherein the presence of the analyte is determined by correlation with the change in intensity of radiation emitted from the donor, and/or, in the event the acceptor is also a fluorophore with the change in radiation emitted from the acceptor.

8. The method according to claim 5, wherein the second chromophore is a fluorophore.

9. The method according to claim 1, wherein determination in step 3 is performed by measuring light emitted.

10. The method according to claim 9, wherein measurement is performed with a spectrophotometer.

11. The method according to claim 10, wherein the spectrophotometer is a fluorometer.

12. The method according to claim 1, wherein the MIPs are used multiple times for determination of the analyte.

13. The method according to claim 12, wherein a determination of analyte is followed by a step of liberation of ligand and analyte from the MIPs so as to enable repeated use.

14. The method according to claim 12, wherein the MIPs are present in a compartment that comprises an inlet for sample and optionally an inlet for ligand, means for liberating ligand and sample from the MIPs, and at least one outlet for liberated sample and optionally for liberated ligand.

15. The method according to claim 1, wherein the ligand is selected from:
 a molecule identical to the analyte or a fragment thereof or a mimic thereof, directly coupled to a label,
 a molecule identical to the analyte of a fragment thereof or a mimic thereof, coupled to a larger carrier molecule to which is also coupled a label, and
 a molecule identical to the analyte or a fragment thereof or a mimic thereof, coupled to both a larger carrier molecule and to a label.

16. The method according to claim 15, wherein the larger carrier molecule is a polysaccharide.

17. The method according to claim 16, wherein the polysaccharide is dextran.

* * * * *